US011919860B1

(12) United States Patent
Venugopala et al.

(10) Patent No.: US 11,919,860 B1
(45) Date of Patent: Mar. 5, 2024

(54) 1-2(-(SUBSTITUTED PHENYL)-2-OXOETHYL)-4-(ISOPROPOXYCARBONYL)PYRIDIN-1-IUM BROMIDES AS ANTI-TUBERCULAR AGENTS

(71) Applicant: KING FAISAL UNIVERSITY, Al-Ahsa (SA)

(72) Inventors: Katharigatta N. Venugopala, Al-Ahsa (SA); Pran Kishore Deb, Ranchi (IN); Melendran Pillay, Durban (ZA); Mohamed A. Morsy, Al-Ahsa (SA); Bandar Aldhubiab, Al-Ahsa (SA); Sandeep Chandrashekharappa, Lucknow (IN)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/377,542

(22) Filed: Oct. 6, 2023

(51) Int. Cl.
*C07D 213/79* (2006.01)
*A61P 31/06* (2006.01)

(52) U.S. Cl.
CPC ............ *C07D 213/79* (2013.01); *A61P 31/06* (2018.01)

(58) Field of Classification Search
CPC ................................ C07D 213/79; A61P 31/06
See application file for complete search history.

(56) References Cited

U.S. PATENT DOCUMENTS

| | | |
|---|---|---|
| 5,480,892 A | 1/1996 | Ciganek et al. |
| 2002/0103228 A1 | 8/2002 | Sankaranarayanan |

FOREIGN PATENT DOCUMENTS

| | | |
|---|---|---|
| AU | 2011330996 A1 | 11/2010 |
| EP | 0497843 A1 | 5/1991 |
| EP | 1304101 A1 | 10/2001 |
| JP | 09194816 A | 7/1997 |

OTHER PUBLICATIONS

Huang et al., 17(2) Molecular Diversity 221-243 (2013) (Year: 2013).*
Venugopala et al., "Anti-Tubercular Activity of Substituted 7-Methyl and 7-Formylindolizines and in Silico Study for Prospective Molecular Target Identification", Antibiotics 2019, 8, 247.
Venugopala et al. "Anti-tubercular activity and molecular docking studies of indolizine derivatives targeting mycobacterial InhA enzyme", J Enzyme Inhib Med Chem. Dec. 2021;36(1):1472-1487.

* cited by examiner

*Primary Examiner* — Timothy R Rozof
(74) *Attorney, Agent, or Firm* — Nath, Goldberg & Meyer; Richard C. Litman

(57) ABSTRACT

Novel 1-(2-(substituted phenyl)-2-oxoethyl)-4-(isopropoxycarbonyl)pyridin-1-ium bromide derivatives, a method of synthesizing said compounds, a pharmaceutical composition comprising said compounds and a suitable carrier, and a method of using the compounds. The 1-(2-(substituted phenyl)-2-oxoethyl)-4-(isopropoxycarbonyl)pyridin-1-ium bromide derivative compounds are useful as anti-tubercular agents.

16 Claims, No Drawings

1-2(-(SUBSTITUTED PHENYL)-2-OXOETHYL)-4-(ISOPROPOXYCARBONYL)PYRIDIN-1-IUM BROMIDES AS ANTI-TUBERCULAR AGENTS

BACKGROUND

1. FIELD

The present disclosure provides novel 1-(2-(substituted phenyl)-2-oxoethyl)-4-(isopropoxycarbonyl)pyridin-1-ium bromide derivatives as anti-tubercular agents, compositions containing such compounds, and methods of their preparation.

2. DESCRIPTION OF THE RELATED ART

Tuberculosis (TB) is a communicable infectious disease and a major cause of illness, particularly in low-income countries. It is caused by the opportunistic bacillus *Mycobacterium tuberculosis* (MTB), which primarily attacks the lungs (pulmonary), but may later affect other parts (extrapulmonary) of the body. Several factors have contributed to the continuous health threat of TB globally, including the development of drug resistance, such as multidrug-resistant tuberculosis (MDR-TB), extensively drug-resistant tuberculosis (XDR-TB), and totally drug-resistant tuberculosis (TDR-TB); the co-morbidities with acquired immunodeficiency syndrome (AIDS), and the risks involved in developing diabetes mellitus among TB patients. New therapeutic strategies are needed to combat the tuberculosis pandemic and the growing resistance to conventional anti-TB drugs, which remain a serious public health challenge worldwide.

In the past forty years, there are not many novel anti-tubercular (anti-TB) drugs approved except Bedaquiline (Approved in 2012 by US-FDA), Delamanid (Approved in 2014 in Europe), and Pretomanid (Approved in 2019 by US-FDA). These three new drugs are not efficient all alone, and they have always been combined with first-line and second-line anti-TB drugs and come with serious side effects. Further, clinical resistance to conventional anti-TB drugs has been widely reported in extensively drug-resistant tuberculosis (XDR-TB) patients.

Thus, antitubercular compounds solving the aforementioned problems are desired.

SUMMARY

In an effort in the process of discovering a novel anti-TB agent with a new molecular mechanism of action, a series of 1-(2--(substituted phenyl)-2-oxoethyl)-4-(isopropoxycarbonyl)pyridin-1-ium bromide derivatives have been achieved by synthetic chemical method. These compounds are evaluated for anti-TB activity against *Mycobacterium tuberculosis* H37Rv, multi-drug resistant (MDR), and extensively drug-resistant tuberculosis (XDR) strains of *Mycobacterium tuberculosis*. Some compounds show promising anti-tubercular activity at millimolar to micromolar concentrations when tested alone against whole-cell *Mycobacterium tuberculosis* organisms. Some of the selected lead compounds can be successfully taken forward to develop novel anti-TB drug candidates.)

Accordingly, the present subject matter provides novel 1-(2-(substituted phenyl)-2-oxoethyl)-4-(isopropoxycarbonyl)pyridin-1-ium bromide derivatives as anti-tubercular agents. The present subject matter further provides a process for the synthesis of such compounds, pharmaceutical compositions containing these compounds, and their use in therapy for the treatment of tuberculosis as a sole active agent or in combination with other active ingredients.

In an embodiment, the present subject matter relates to a compound having the formula I:

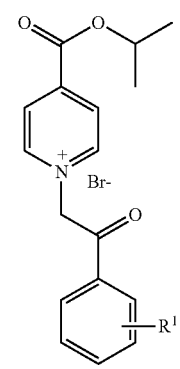

or a pharmaceutically acceptable salt, ester, stereoisomer, or solvate thereof, wherein:

$R^1$ is selected from the group consisting of a halogen, —CN, and methyl.

In another embodiment, the present subject matter relates to a method of treating tuberculosis in a patient comprising administering to a patient in need thereof a therapeutically effective amount of a compound having the formula I:

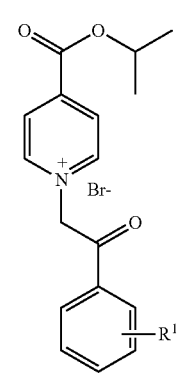

or a pharmaceutically acceptable salt, ester, stereoisomer, or solvate thereof, wherein:

$R^1$ is selected from the group consisting of hydrogen, a halogen, —CN, and methyl.

In an embodiment, the present subject matter relates to a compound, or a method of treating tuberculosis using a compound, selected from the group consisting of: 4-(Isopropoxycarbonyl)-1-(2-oxo-2-phenylethyl)pyridin-1-ium bromide (4a); 1-(2-(4-Fluorophenyl)-2-oxoethyl)-4-(isopropoxycarbonyl)pyridin-1-ium bromide (4b); 1-(2-(4-Chlorophenyl)-2-oxoethyl)-4-(isopropoxycarbonyl)pyridin-1-ium bromide (4c); 1-(2-(4-Bromophenyl)-2-oxoethyl)-4-(isopropoxycarbonyl)pyridin-1-ium bromide (4d); 1-(2-(4-Cyanophenyl)-2-oxoethyl)-4-(isopropoxycarbonyl)pyridin-1-ium bromide (4e); 4-(Isopropoxycarbonyl)-1-(2-oxo-2-(p-tolyl)ethyl)pyridin-1-ium bromide (4f); and a pharmaceutically acceptable salt, ester, stereoisomer, or solvate thereof.

In an embodiment, the present subject matter relates to a process for the synthesis of the compounds of formula I, including a number of species or specific structures falling under structural formula I. Further contemplated herein are pharmaceutical compositions containing these compounds, as well as methods of treating tuberculosis by administering the present compounds to a patient in need thereof.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.)

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

As used herein, "halo" or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl, -pentyl), hexyl groups, and the like. In various embodiments, an alkyl group can have 1 to 40 carbon atoms (i.e., $C_1$-$C_{40}$ alkyl group), for example, 1-30 carbon atoms (i.e., $C_1$-$C_{30}$ alkyl group). In some embodiments, an alkyl group can have 1 to 6 carbon atoms, and can be referred to as a "lower alkyl group" or a "$C_1$-$C_6$ alkyl group". Examples of lower alkyl groups include methyl, ethyl, propyl (e.g., n-propyl and z'-propyl), and butyl groups (e.g., n-butyl, z'-butyl, sec-butyl, tert-butyl.). In some embodiments, alkyl groups can be substituted as described herein. An alkyl group is generally not substituted with another alkyl group, an alkenyl group, or an alkynyl group.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_2$-$C_{40}$ alkenyl group), for example, 2 to 20 carbon atoms (i.e., $C_2$-$C_{20}$ alkenyl group) or 2 to 6 carbon atoms (i.e., $C_2$-$C_6$ alkenyl group). In some embodiments, alkenyl groups can be substituted as described herein. An alkenyl group is generally not substituted with another alkenyl group, an alkyl group, or an alkynyl group.

The term "substituted alkyl" as used herein refers to an alkyl group in which 1 or more (up to about 5, for example about 3) hydrogen atoms is replaced by a substituent independently selected from the group: —O, —S, acyl, acyloxy, optionally substituted alkoxy, optionally substituted amino (wherein the amino group may be a cyclic amine), azido, carboxyl, (optionally substituted alkoxy)carbonyl, amido, cyano, optionally substituted cycloalkyl, optionally substituted cycloalkenyl, halogen, hydroxyl, nitro, sulfamoyl, sulfanyl, sulfinyl, sulfonyl, and sulfonic acid. Some of the optional substituents for alkyl are hydroxy, halogen exemplified by chloro and bromo, acyl exemplified by methylcarbonyl; alkoxy, and heterocyclyl exemplified by morpholino and piperidino. Other alkyl substituents as described herein may further be contemplated.

The term "substituted alkenyl" refers to an alkenyl group in which 1 or more (up to about 5, for example about 3) hydrogen atoms is replaced by a substituent independently selected from those listed above with respect to a substituted alkyl. Other alkenyl substituents as described herein may further be contemplated.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., $C_6$-$C_{24}$ aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —C6F5), are included within the definition of "haloaryl". In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—0 bonds. However, one or more N or S atoms in a heteroaryl group can be oxidized (e.g., pyridine N-oxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), $SiH_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined herein.

It will be understood by those skilled in the art with respect to any chemical group containing one or more substituents that such groups are not intended to introduce any substitution or substitution patterns that are sterically impractical and/or physically on-feasible.

The term "isomers" or "stereoisomers" as used herein relates to compounds that have identical molecular formulae but that differ in the arrangement of their atoms in space. Stereoisomers that are not mirror images of one another are termed "diastereoisomers" and stereoisomers that are non-superimposable mirror images are termed "enantiomers," or sometimes optical isomers. A carbon atom bonded to four non-identical substituents is termed a "chiral center." Certain compounds herein have one or more chiral centers and therefore may exist as either individual stereoisomers or as a mixture of stereoisomers. Configurations of stereoisomers that owe their existence to hindered rotation about double bonds are differentiated by their prefixes cis and trans (or Z and E), which indicate that the groups are on the same side (cis or Z) or on opposite sides (trans or E) of the double bond in the molecule according to the Cahn-Ingold-Prelog rules. All possible stereoisomers are contemplated herein as individual stereoisomers or as a mixture of stereoisomers.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as a microbial infection, or tuberculosis.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an effort in the process of discovering a novel anti-TB agent with a new molecular mechanism of action, a series of 1-(2-(substituted phenyl)-2-oxoethyl)-4-(isopropoxycarbonyl)pyridin-1-ium bromide derivatives have been achieved by synthetic chemical method. These compounds are evaluated for anti-TB activity against *Mycobacterium tuberculosis* H37Rv, multi-drug resistant (MDR), and extensively drug-resistant tuberculosis (XDR) strains of *Mycobacterium tuberculosis*. Some compounds show promising anti-tubercular activity at millimolar to micromolar concentrations when tested alone against whole-cell *Mycobacterium tuberculosis* organisms. Some of the selected lead compounds can be successfully taken forward to develop novel anti-TB drug candidates.

Accordingly, the present subject matter provides novel 1-(2-(substituted phenyl)-2-oxoethyl)-4-(isopropoxycarbonyl)pyridin-1-ium bromide derivatives as anti-tubercular agents. The present subject matter further provides a process for the synthesis of such compounds, pharmaceutical compositions containing these compounds, and their use in therapy for the treatment of tuberculosis as a sole active agent or in combination with other active ingredients.

In an embodiment, the present subject matter relates to a compound having the formula I:

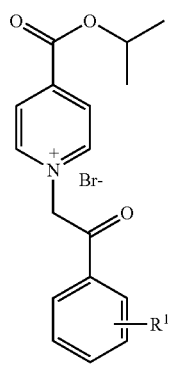

I or a pharmaceutically acceptable salt, ester, stereoisomer, or solvate thereof, wherein:

$R^1$ is selected from the group consisting of a halogen, —CN, and methyl.

In a further embodiment, the present subject matter relates to compounds of formula I, wherein $R^1$ can be a fluorine, chlorine, bromine, —CN, or methyl.

In another embodiment, the $R^1$ group can be attached at the 4-position of the phenyl ring.

In another embodiment, the present subject matter relates to a method of treating tuberculosis in a patient comprising administering to a patient in need thereof a therapeutically effective amount of a compound having the formula I:

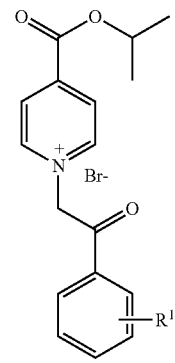

I or a pharmaceutically acceptable salt, ester, stereoisomer, or solvate thereof, wherein:

$R^1$ is selected from the group consisting of hydrogen, a halogen, —CN, and methyl.

In a further embodiment, the present subject matter relates to methods of treating tuberculosis, wherein, in the compounds of formula I, $R^1$ can be a fluorine, chlorine, bromine, —CN, or methyl.

In a further embodiment, the present subject matter relates to methods of treating tuberculosis, wherein, in the compounds of formula I, the $R^1$ group can be attached at the 4-position of the phenyl ring.

In an embodiment, the present subject matter relates to a compound, or a method of treating tuberculosis using a compound. selected from the group consisting of: 4-(Isopropoxycarbonyl)-1-(2-oxo-2-phenylethyl)pyridin-1-ium bromide (4a); 1-(2-(4-Fluorophenyl)-2-oxoethyl)-4-(isopropoxycarbonyl)pyridin-1-ium bromide (4b); 1-(2-(4-Chlorophenyl)-2-oxoethyl)-4-(isopropoxycarbonyl)pyridin-1-ium bromide (4c); 1-(2-(4-Bromophenyl)-2-oxoethyl)-4-(isopropoxycarbonyl)pyridin-1-ium bromide (4d); 1-(2-(4-Cyanophenyl)-2-oxoethyl)-4-(isopropoxycarbonyl)pyridin-1-ium bromide (4e); 4-(Isopropoxycarbonyl)-1-(2-oxo-2-(p-tolyl)ethyl)pyridin-1-ium bromide (4f); and a pharmaceutically acceptable salt, ester, stereoisomer, or solvate thereof.

Said differently, the present subject matter can relate to compounds of formula I selected from the group consisting of:

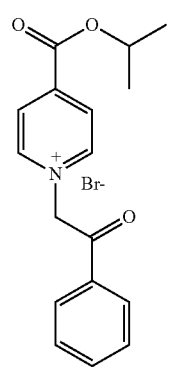

4a

-continued

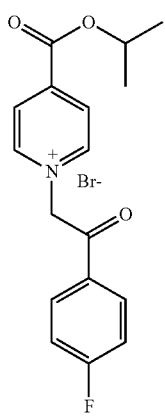
4b

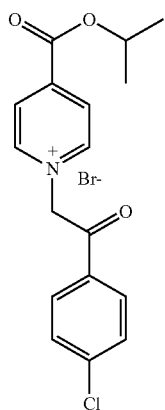
4c

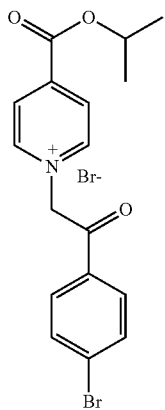
4d

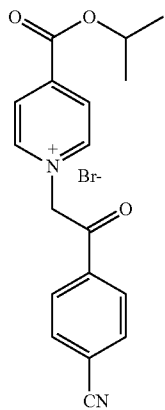
4e

-continued

4f and a pharmaceutically acceptable salt, ester, stereoisomer, or solvate thereof.

It is to be understood that the present subject matter covers all combinations of substituent groups referred to herein.

The present compounds may contain, e.g., when isolated in crystalline form, varying amounts of solvents. Accordingly, the present subject matter includes all solvates of the present compounds of formula I and pharmaceutically acceptable stereoisomers, esters, and/or salts thereof. Hydrates are one example of such solvates.

Further, the present subject matter includes all mixtures of possible stereoisomers of the embodied compounds, independent of the ratio, including the racemates.

Salts of the present compounds, or salts of the stereoisomers thereof, include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phosphates, nitrates, sulfates, acetates, trifluoroacetates, citrates, D-gluconates, benzoates, 2-(4-hydroxy-benzoyl)benzoates, butyrates, subsalicylates, maleates, laurates, malates, lactates, fumarates, succinates, oxalates, tartrates, stearates, benzenesulfonates (besilates), toluenesulfonates (tosilates), methanesulfonates (mesilates) and 3-hydroxy-2-naphthoates.

Examples of salts with bases include, but are not limited to, lithium, sodium, potassium, calcium, aluminum, magnesium, titanium, ammonium, meglumine and guanidinium salts. The salts include water-insoluble and, particularly, water-soluble salts.

The present compounds, the salts, the stereoisomers and the salts of the stereoisomers thereof may contain, e.g., when isolated in crystalline form, varying amounts of solvents. Included within the present scope are, therefore, all solvates of the compounds of formula I, as well as the solvates of the salts, the stereoisomers and the salts of the stereoisomers of the compounds of formula I.

The present compounds may be isolated and purified in a manner known per se, e.g., by distilling off the solvent in vacuo and recrystallizing the residue obtained from a suitable solvent or subjecting it to one of the customary purification methods, such as column chromatography on a suitable support material.

Salts of the compounds of formula I and the stereoisomers thereof can be obtained by dissolving the free compound in a suitable solvent (by way of non-limiting example, a ketone such as acetone, methylethylketone or methylisobutylketone; an ether such as diethyl ether, tetrahydrofurane or dioxane; a chlorinated hydrocarbon such as methylene chloride or chloroform; a low molecular weight aliphatic alcohol such as methanol, ethanol or isopropanol; a low molecular weight aliphatic ester such as ethyl acetate or isopropyl acetate; or water) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the present compounds can be obtained, e.g., by asymmetric synthesis, by using chiral starting compounds in synthesis and by splitting up enantiomeric and diastereomeric mixtures obtained in synthesis. Preferably, the pure diastereomeric and pure enantiomeric compounds are obtained by using chiral starting compounds in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated, e.g., by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is enzymatic separation.

In one embodiment, the present compounds can be prepared according to the following general synthetic pathway. Specifically, synthesis can commence with refluxing a stirred solution of isonicotinic acid 1 in isopropanol with a few drops of concentrated sulphuric acid. The completion of the reaction is monitored by TLC. The isopropanol is evaporated under vacuum and the crude product is diluted with ethyl acetate. The ethyl acetate is washed with saturated sodium bicarbonate, brine and dried with anhydrous sodium sulphate. The solvent is evaporated to obtain compound 2.

The pathway continues with stirring a solution of compound 2 in acetone and substituted phenacyl bromide at room temperature for at least about 24 hours. The completion of the reaction is monitored by TLC. Solids are filtered and dried under vacuum to obtain compounds 4a-4f. The purification of the compound is achieved by a recrystallization method.

The overall synthetic strategy adopted is illustrated in Scheme 1:

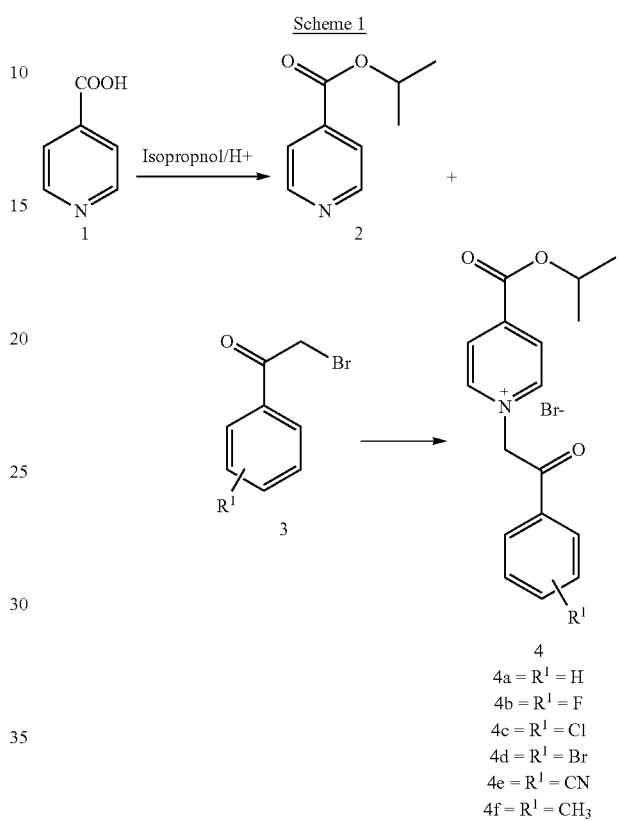

In another embodiment, the present subject matter is directed to pharmaceutical compositions comprising a therapeutically effective amount of the compounds as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises at least one of the present compounds together with at least one pharmaceutically acceptable auxiliary.

In an embodiment, the pharmaceutical composition comprises one or two or more of the present compounds, or one of the present compounds.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compounds are typically administered at a therapeutically or pharmaceutically effective dosage, e.g., a dosage sufficient to provide treatment for tuberculosis. Administration of the compounds or pharmaceutical compositions thereof can be by any method that delivers the compounds systemically and/or locally. These methods include oral routes, parenteral routes, intraduodenal routes, and the like.

While human dosage levels have yet to be optimized for the present compounds, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compounds for treatment of tuberculosis, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for humans or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of a compound or salt of the present compounds, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained release formulations acid the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinyl pyrrolidine, gelatin, cellulose, and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a :liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly, or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

The antitubercular activity of the designed compounds 4a and 4b was evaluated against three types of MTB strains, namely H37Rv and well-characterised MDR and XDR strains using the colorimetric Resazurin Microplate Assay (REMA) method. A positive reaction resulted in a color change from blue to pink owing to the reduction of resazurin to rezarufin which confirmed MTB cell viability/growth and, hence, drug resistance. The MICS were defined as the minimum drug concentration to inhibit the growth of the organism with no colour changes present in the well.

In one embodiment, a present compound 4a engaged for in vitro study against *Mycobacterium tuberculosis* can display a minimum inhibitory concentration (MIC) of 0.5 µg/mL against the H37Rv strain of *Mycobacterium Tuberculosis* (MTB), a MIC of 2 µg/mL against the MDR strain of MTB where MDR is drug resistance to at least isoniazid and rifampicin, known tuberculosis drugs, and a MIC of 2 µg/mL where XDR is extensively drug resistance to isoniazid, rifampicin, and additional resistance to a fluoroquinolone and a second-line injectable. It is anticipated the other compounds described herein will have similar results.

In another embodiment, a present compound 4b engaged for in vitro study against *Mycobacterium tuberculosis* can display a minimum inhibitory concentration (MIC) of 1 µg/mL against the H37Rv strain of MTB, a MIC of 1 µg/mL against the MDR strain of MTB where MDR is drug resistance to at least isoniazid and rifampicin, known tuberculosis drugs, and a MIC of 16 µg/mL where XDR is extensively drug resistance to isoniazid, rifampicin, and additional resistance to a fluoroquinolone and a second-line injectable. It is anticipated the other compounds described herein will have similar results.

The present subject matter further relates to a method of treating or preventing a disease comprising administering to a patient in need thereof a therapeutically effective amount of at least one of the compounds herein.

In particular, the present subject matter relates to a method of treating one of the above-mentioned diseases or disorders comprising administering to a patient need thereof a therapeutically effective amount of at least one of the compounds herein.

In the above methods, the patient is preferably a mammal, more preferably a human. Furthermore, in the above methods, at least one of the present compounds can be used. In an embodiment, one or two of the present compounds are used, or one of the present compounds is used. Similarly, one or more of the present compounds can be used in combination therapy with one or more additional active agents.

The following examples relate to various methods of manufacturing certain specific compounds as described herein. All compound numbers expressed herein are with reference to the synthetic pathway figures shown above.

EXAMPLES

Example 1

Synthesis of Isopropyl Isonicotinate (2)

A stirred solution of isonicotinic acid 1 in isopropanol was refluxed with a few drops of concentrated sulphuric acid. The completion of the reaction was monitored by TLC. Evaporate the isopropanol under vacuum, dilute the crude product with ethyl acetate, and wash the ethyl acetate with saturated sodium bicarbonate, brine and dried with anhydrous sodium sulphate and evaporate the solvent to get compound 2.

Example 2

General Procedure for the Synthesis of 1-(2-(substituted phenyl)-2-oxoethyl)-4-(isopropoxycarbonyl) pyridin-1-ium Bromides (4a-4f)

To a stirred solution of compound 2 in acetone and substituted phenacyl bromide 3 was stirred at room temperature 24 hours. The completion of reaction was monitored by TLC. Solids were filtered and dried under vacuum to obtain compound 4a-4f. The purification of the compound was achieved by recrystallization method.

Example 3

4-(Isopropoxycarbonyl)-1-(2-oxo-2-phenylethyl) pyridin-1-ium Bromide (4a)

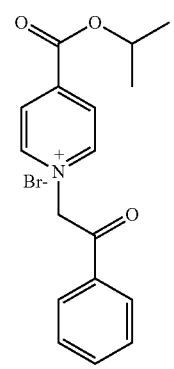

4a

¹H NMR (500 MHz, CDCl₃) δ 9.57 (d, J=6.0 Hz, 2H), 8.46 (d, J=5.9 Hz, 2H), 8.15 (d, J=7.7 Hz, 2H), 7.63 (t, J=7.4 Hz, 1H), 7.49 (t, J=7.6 Hz, 2H), 7.38 (s, 2H), 5.38 (m, 1H), 1.46 (d, J=6.2 Hz, 6H): ¹³C NMR (125 MHz, CDCl₃) δ 189.74, 160.81, 148.05, 145.49, 135.04, 133.24, 129.27, 129.00, 126.63, 72.29, 67.47, 21.73. Mass: (M+H)=363.0470.

Example 4

1-2-(4-Fluorophenyl)-2-oxoethyl)-4-(isopropoxycarbonyl)pyridin-1-ium Bromide (4b)

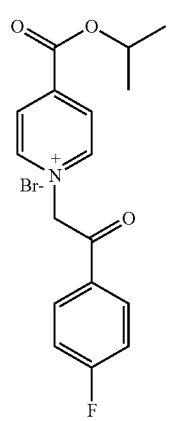

4b

¹H NMR (500 MHz, CDCl₃) δ 9.56 (d, J=6.1 Hz, 2H), 8.48 (d, J=6.1 Hz, 2H), 8.24 (dd, J=8.6, 5.1 Hz, 2H), 7.44 (s, 2H), 7.18 (t, J=8.3 Hz, 2H), 5.45-5.35 (m, 1H), 1.47 (d, J=6.3 Hz, 6H); ¹³C NMR (125 MHz, CDCl₃) δ 188.27, 160.71, 147.97, 145.64, 132.06, 131.99, 126.67, 116.67, 116.49, 72.43, 67.31, 21.71; Mass: (M+H)=302.1220.

Example 5

1-(2-(4-Chlorophenyl)-2-oxoethyl)-4-(isopropoxycarbonyl)pyridin-1-ium Bromide (4c)

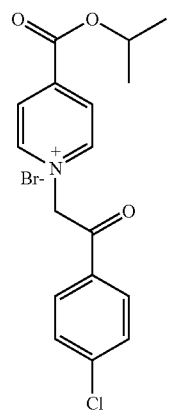

4c

¹H NMR (500 MHz, CDCl₃) δ 9.57 (d, J=6.1 Hz, 2H), 8.45 (d, J=6.0 Hz, 2H), 8.11 (d, J=8.2 Hz, 2H), 7.43 (d, J=8.1 Hz, 2H), 7.39 (s, 2H), 5.38-5.35 (m, 1H), 1.45 (d, J=6.3 Hz, 6H): ¹³C NMR (125 MHz, CDCl₃) δ 206. 188.83, 160.75, 147.96, 145.58, 141.56, 131.59, 130.47, 129.54, 126.69, 72.33, 67.31, 21.71; Mass: (M+H)=318.0910.

Example 6

1-(2-(4-Bromophenyl)-2-oxoethyl)-4-(isopropoxycarbonyl)pyridin-1-ium Bromide (4d)

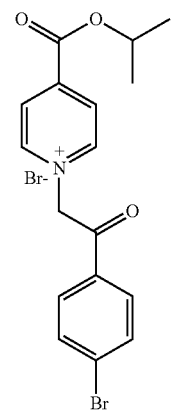

4d

¹H NMR (500 MHz, CDCl₃) δ 9.58 (d, J=6.1 Hz, 2H), 8.46 (d, J=5.8 Hz, 2H), 8.04 (d, J=8.2 Hz, 2H), 7.60 (d, J=8.0 Hz, 2H), 7.40 (s, 2H), 5.40-5.34 (m, 1H), 1.46 (d, J=6.3 Hz, 6H). ¹³C NMR (125 MHz, CDCl₃) δ 206.99, 189.08, 160.75, 147.96, 145.59, 132.55, 131.99, 130.49, 126.70, 72.34, 67.29, 30.92, 21.72; Mass: (M+H)=362.0383.

Example 7

1-(2-(4-Cyanophenyl)-2-oxoethyl)-4-(isopropoxycarbonyl)pyridin-1-ium Bromide (4e)

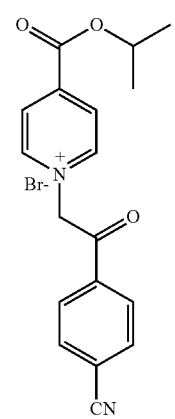

4e

¹H NMR (500 MHz, CDCl₃) δ 9.58 (d, J=6.0 Hz, 2H), 8.50 (d, J=5.6 Hz, 2H), 8.32 (d, J=8.0 Hz, 2H), 7.79 (d, J=7.9 Hz, 2H), 7.56 (s, 2H), 5.43-5.38 (m, 1H), 1.48 (d, J=6.3 Hz, 6H). ¹³C NMR (125 MHz, CDCl₃) δ 189.15, 160.63, 147.90, 145.95, 136.20, 132.92, 129.60, 126.89, 117.93, 72.62, 67.64, 21.74; Mass: (M+H)=389.2490.

Example 8

4-(Isopropoxycarbonyl)-1-(2-oxo-2-(p-tolyl)ethyl) pyridin-1-ium Bromide (4f)

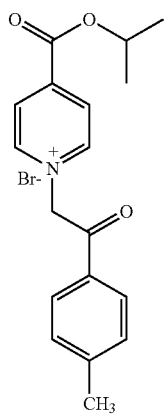

$^1$H NMR (500 MHz, CDCl$_3$) δ 9.54 (d, J=6.0 Hz, 2H), 8.47 (d, J=5.8 Hz, 2H), 8.29 (d, J=7.6 Hz, 1H), 8.05 (d, J=7.7 Hz, 2H), 7.41 (d, J=8.2 Hz, 1H), 7.29-7.28 (m, 2H), 5.38-5.34 (m, 1H), 2.42 (s, 3H), 1.46 (dd, J=6.3, 1.5 Hz, 6H). $^{13}$C NMR (125 MHz, CDCl$_3$) δ 189.11, 160.82, 148.03, 147.01, 146.39, 145.43, 131.04, 130.70, 130.20, 129.96, 129.11, 126.83, 126.61, 72.28, 67.36, 21.72; Mass: (M+H)=298.1381.

Pharmacological Activity

Example 9

Anti-tubercular Activity

The antitubercular activity of the representative title compounds 4-(isopropoxycarbonyl)-1(2-oxo-2-phenylethyl) pyridin-1-ium bromide (4a) and 1-(2-(4-fluorophenyl)-2-oxoethyl)-4-(isopropoxycarbonyl)pyridin-1-ium bromide (4b) were evaluated against two types of MTB strains, namely H37Rv and well characterised MDR and XDR strains using the colorimetric Resazurin Microplate Assay (REMA) method. A 100 mL of Middlebrook 7H9 broth was aseptically prepared and dispensed in each of the wells of a 96 well flat-bottomed microtiter plate with lids (Lasec, South Africa). Each of the test compounds was accurately weighed, dissolved in the appropriate solvent, and filter sterilised using a 0.2 micron polycarbonate filter. Stock solutions of the test samples were aliquoted into cryovials and stored at −20° C. A 100 mL of the test samples were added to each of the wells containing Middlebrook 7H9 broth supplemented with 0.1% Casitone, 0.5% glycerol, and 10% OADC (oleic acid, albumin, dextrose, and catalase). The test samples were then serially diluted two folds directly in the broth of the microtiter plate to the desired concentration ranging from 40-0.625 mg/mL. Inoculums from clinical isolates were prepared fresh from Middlebrook 7H11 agar plates by scraping and re-suspending loopful of colonies into Middlebrook 7H9 broth containing glass beads. The inoculum turbidity was adjusted to a McFarland number 1 standard and further diluted to 1:10 in M7H9 broth prior to the addition of 100 mL to each of the test samples and drug-free wells. Growth control and a sterile control were also included for each isolate. Sterile M7H9 broth was added to all perimeter walls to avoid evaporation during the incubation. The plate was covered, sealed in a plastic bag, and incubated at 37° C. After 8 days of incubation, 30 mL of 0.02% working solution of resazurin salt was inoculated into each microtiter well. The plates were then incubated overnight and read the following day. A positive reaction resulted in a colour change from blue to pink owing to the reduction of resazurin to rezarufin which confirmed MTB cell viability/growth and, hence, drug resistance. The MICs were defined as the minimum drug concentration to inhibit the growth of the organism with no colour changes present in the well.

Anti-tubercular results of the representative title compounds 4-(isopropoxycarbonyl)-1-(2-oxo-2-phenylethyl) pyridin-1-ium bromide (4a) and 1-(2-(4-fluorophenyl)-2-oxoethyl)-4-(isopropoxycarbonyl)pyridin-1-ium bromide (4b) against *Mycobacterium tuberculosis* is presented in Table 1.

By way of example, the compounds (4a) and (4b) displayed promising anti-tubercular activity against *Mycobacterium tuberculosis* as reported in Table 1.

TABLE 1

Anti-tubercular results of the representative title compounds 4a, and 4b in μg/mL.

| Compound code | Compound Structure | Anti-tubercular activity against *Mycobacterium tuberculosis* (μg/mL) | | |
|---|---|---|---|---|
| | | H37Rv[1] | MDR[2] | XDR[3] |
| 4a | 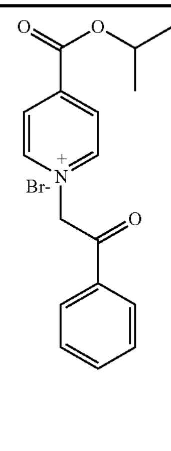 | 0.5 | 2 | 2 |

TABLE 1-continued

Anti-tubercular results of the representative title compounds 4a, and 4b in μg/mL.

| Compound code | Compound Structure | Anti-tubercular activity against *Mycobacterium tuberculosis* (μg/mL) | | |
|---|---|---|---|---|
| | | H37Rv[1] | MDR[2] | XDR[3] |
| 4b | 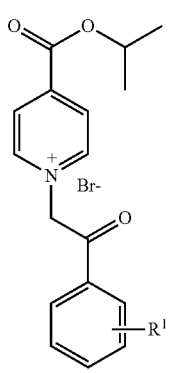 | 1 | 1 | 16 |

[1]ATCC: 25177

[2]Multi-drug resistant TB (MDR-TB) = drug resistance at least to isoniazid and rifampicin

[3]Extensively drug-resistance TB or XDR-TB (i.e. MTB resistance to isoniazid, rifampicin, and additional resistance to a fluoroquinolone and a second-line injectable)

It is to be understood that the 1-(2-(substituted phenyl)-2-oxoethyl)-4-(isopropoxycarbonyl)pyridin-1-ium bromide derivatives are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A compound having the formula I:

I or a pharmaceutically acceptable salt, ester, stereoisomer, or solvate thereof, wherein:
   $R^1$ is selected from the group consisting of a halogen —CN, and methyl.

2. The compound of claim 1, wherein $R^1$ is selected from the group consisting of flourine, chlorine, bromine, —CN, and methyl.

3. The compound of claim 2, wherein $R^1$ is at the 4-position of the phenyl ring.

4. The compound of claim 1, wherein the compound is selected from the group consisting of:
   1-(2-(4-Fluorophenyl)-2-oxoethyl)-4-(isopropoxycarbonyl)pyridin-1-ium bromide (4b);
   1-(2-(4-Chlorophenyl)-2-oxoethyl)-4-(isopropoxycarbonyl)pyridin-1-ium bromide (4c);
   1-(2-(4-Bromophenyl)-2-oxoethyl)-4-(isopropoxycarbonyl)pyridin-1-ium bromide (4d);
   1-(2-(4-Cyanophenyl)-2-oxoethyl)-4-(isopropoxycarbonyl)pyridin-1-ium bromide (4e);
   4-(Isopropoxycarbonyl)-1-(2-oxo-2-(p-tolyl)ethyl)pyridin-1-ium bromide (4f);
   and a pharmaceutically acceptable salt, ester, stereoisomer, or solvate thereof.

5. A pharmaceutically acceptable composition comprising a therapeutically effective amount of the compound of claim 1 and a pharmaceutically acceptable carrier.

6. A method of treating tuberculosis in a patient, comprising administering to a patient in need thereof a therapeutically effective amount of the compound of claim 1.

7. The method of treating tuberculosis according to claim 6, wherein the tuberculosis is selected from the group consisting of one or more of a H37Rv strain of *Myobacterium Tuberculosis* (MTB), a MDR strain of MTB, and an XDR strain of MTB.

8. A method of treating tuberculosis in a patient comprising administering to a patient in need thereof a therapeutically effective amount of a compound having the formula I:

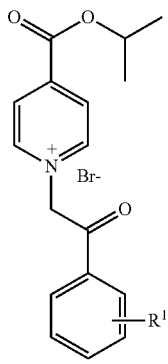

or a pharmaceutically acceptable salt, ester, stereoisomer, or solvate thereof, wherein:
$R^1$ is selected from the group consisting of hydrogen, a halogen, —CN, and methyl.

9. The method of treating tuberculosis of claim 8, wherein $R^1$ is selected from the group consisting of hydrogen, fluorine, chlorine, bromine, —CN, and methyl.

10. The method of treating tuberculosis of claim 9, wherein $R^1$ is at the 4-position of the phenyl ring.

11. The method of treating tuberculosis of claim 8, wherein the compound is selected from the group consisting of:
4-(Isopropoxycarbonyl)-1-(2-oxo-2-phenylethyl)pyridin-1-ium bromide (4a);
1-(2-(4-Fluorophenyl)-2-oxoethyl)-4-(isopropoxycarbonyl)pyridin-1-ium bromide (4b);
1-(2-(4-Chlorophenyl)-2-oxoethyl)-4-(isopropoxycarbonyl)pyridin-1-ium bromide (4c);
1-(2-(4-Bromophenyl)-2-oxoethyl)-4-(isopropoxycarbonyl)pyridin-1-ium bromide (4d);
1-(2-(4-Cyanophenyl)-2-oxoethyl)-4-(isopropoxycarbonyl)pyridin-1-ium bromide (4e);
4-(Isopropoxycarbonyl)-1-(2-oxo-2-(p-tolyl)ethyl)pyridin-1-ium bromide (4f);
and a pharmaceutically acceptable salt, ester, stereoisomer, or solvate thereof.

12. The method of treating tuberculosis according to claim 8, wherein the tuberculosis is selected from the group consisting of one or more of a H37Rv strain of *Mycobacterium Tuberculosis* (MTB), a MDR strain of MTB, and a XDR strain of MTB.

13. A compound selected from the group consisting of:
1-(2-(4-Fluorophenyl)-2-oxoethyl)-4-(isopropoxycarbonyl)pyridin-1-ium bromide (4b);
1-(2-(4-Chlorophenyl)-2-oxoethyl)-4-(isopropoxycarbonyl)pyridin-1-ium bromide (4c);
1-(2-(4-Bromophenyl)-2-oxoethyl)-4-(isopropoxycarbonyl)pyridin-1-ium bromide (4d);
1-(2-(4-Cyanophenyl)-2-oxoethyl)-4-(isopropoxycarbonyl)pyridin-1-ium bromide (4e);
4-(Isopropoxycarbonyl)-1-(2-oxo-2-(p-tolyl)ethyl)pyridin-1-ium bromide (4f);
and a pharmaceutically acceptable salt, ester, stereoisomer, or solvate thereof.

14. A pharmaceutically acceptable composition comprising a therapeutically effective amount of the compound of claim 13 and a pharmaceutically acceptable carrier.

15. A method of treating a tuberculosis in a patient, comprising administering to a patient in need thereof a therapeutically effective amount of the compound of claim 13.

16. The method of treating tuberculosis according to claim 15, wherein the tuberculosis is selected from the group consisting of one or more of a H37Rv strain of *Mycobacterium Tuberculosis* (MTB), a MDR strain of MTB, and a XDR strain of MTB.

* * * * *